US008792996B2

(12) United States Patent
Sethna et al.

(10) Patent No.: US 8,792,996 B2
(45) Date of Patent: Jul. 29, 2014

(54) IMPLANTABLE MEDICAL LEAD AND METHOD OF MAKING SAME

(75) Inventors: Dorab N. Sethna, Valencia, CA (US); Sean Matthew Desmond, Moorpark, CA (US); Sergey Safarevich, Valencia, CA (US); Keith Victorine, Sherman Oaks, CA (US); Greg Kampa, Castaic, CA (US)

(73) Assignee: PaceSetter, Inc., Sylmar, CA (US)

( * ) Notice: Subject to any disclaimer, the term of this patent is extended or adjusted under 35 U.S.C. 154(b) by 975 days.

(21) Appl. No.: 12/564,518

(22) Filed: Sep. 22, 2009

(65) Prior Publication Data

US 2011/0071607 A1   Mar. 24, 2011

(51) Int. Cl.
*A61N 1/00* (2006.01)
*A61N 1/05* (2006.01)

(52) U.S. Cl.
CPC .. *A61N 1/05* (2013.01); *A61N 1/056* (2013.01)
USPC .......................................................... 607/122

(58) Field of Classification Search
CPC ...................................................... A61N 1/056
USPC ............................................................ 607/122
See application file for complete search history.

(56) References Cited

U.S. PATENT DOCUMENTS

| 4,484,586 A | * | 11/1984 | McMickle et al. ............ 607/122 |
| 5,016,645 A | | 5/1991 | Williams et al. |
| 6,119,042 A | * | 9/2000 | Verness et al. ................ 607/122 |

* cited by examiner

*Primary Examiner* — Christopher D Koharski
*Assistant Examiner* — Nadia Mahmood (57) ABSTRACT

An implantable medical lead is disclosed herein. The lead may include a longitudinally extending body, an electrical conductor, a tube and an electrical component, such as, for example, an electrode for sensing or pacing, a defibrillation coil, a strain gage, a pressure sensor, a piezoelectric sensor, an integrated chip, an inductor, etc. The body may include a distal end and a proximal end. The electrical conductor may extend through the body between the proximal end and the distal end. The tube may be swaged about an outer circumferential portion of the electrical conductor. The electrical component may be on the body and electrically connected to the tube.

15 Claims, 8 Drawing Sheets

IMPLANTABLE MEDICAL LEAD AND METHOD OF MAKING SAME

FIELD OF THE INVENTION

The present invention relates to medical apparatus and methods. More specifically, the present invention relates to implantable medical leads and methods of manufacturing such leads.

BACKGROUND OF THE INVENTION

Implantable pulse generators, such as pacemakers, defibrillators, implantable cardioverter defibrillators ("ICD") and neurostimulators, provide electrotherapy via implantable medical leads to nerves, such as those nerves found in cardiac tissue, the spinal column, the brain, etc. Electrotherapy is provided in the form of electrical signals, which are generated in the pulse generator and travel via the lead's conductors to the electrotherapy treatment site.

Patients may benefit from electrotherapy treatments to be proposed in the future. However, current conventional lead manufacturing technology has generally limited the extent to which leads can be reduced in size and the elements or features that can be carried on leads.

There is a need in the art for a lead having a configuration that allows the lead to have a reduced size and which is capable of supporting elements or features in a variety of configurations. There is also a need in the art for a method of manufacturing such a lead.

BRIEF SUMMARY OF THE INVENTION

An implantable medical lead is disclosed herein. In one embodiment, the lead may include a longitudinally extending body, an electrical conductor, a tube and an electrical component, such as, for example, an electrode for sensing or pacing, a defibrillation coil, a strain gage, a pressure sensor, a piezoelectric sensor, an integrated chip, an inductor, etc. The body may include a distal end and a proximal end. The electrical conductor may extend through the body between the proximal end and the distal end. The tube may be swaged about an outer circumferential portion of the electrical conductor. The electrical component may be on the body and electrically connected to the tube.

A method of assembling an implantable medical lead is also disclosed herein. In one embodiment, the method includes: providing a tube segment; extending an electrical conductor through a lumen of the tube segment; swaging the tube segment about an outer circumferential surface of the electrical conductor; and electrically connecting the tube segment to an electrical component, such as, for example, an electrode for sensing or pacing, a defibrillation coil, a strain gage, a pressure sensor, a piezoelectric sensor, an integrated chip, an inductor, etc.

Another method of assembling an implantable medical lead is also disclosed herein. In one embodiment, the method includes: a) providing multiple tube segments, each tube segment having a lumen; b) extending an electrical conductor through the lumens of the tube segments; c) swaging the tube segments about an outer circumferential surface of the electrical conductor, the tube segments being located along the electrical conductor in a spaced-apart fashion; d) storing the electrical conductor resulting from step (c); e) determining a length of the electrical conductor appropriate for the lead being assembled; f) removing the determined length of the electrical conductor from the stored electrical conductor of step (d); g) extending the determined length of the electrical conductor through a lumen of a lead body; and h) electrically connecting at least one of the multiple tube segments to a corresponding electrical component (e.g., an electrode for sensing or pacing, a defibrillation coil, a strain gage, a pressure sensor, an integrated chip, a piezoelectric sensor, an inductor, etc.) coupled to the lead body.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

An implantable medical lead 10 is disclosed herein. In one embodiment, the implantable medical lead 10 includes a longitudinally extending body 50, an electrical conductor 100, a tube 120 and an electrical component, such as, for example, an electrode 80 for sensing or pacing, a defibrillation coil, a strain gage, a pressure sensor, a piezoelectric sensor, an integrated chip, an inductor, etc. The body 50 may include a distal end 45 and a proximal end 40. The electrical conductor 100 may extend through the body 50 between the proximal end 40 and the distal end 45. The tube 120 may be swaged about an outer circumferential portion of the electrical conductor 100. The electrical component 80 may be on the body 50 and electrically connected to the tube 120. The swaging of the tube 120 to the electrical conductor 100 provides a number of benefits, including facilitating lead designs having reduced diameters and reducing manufacturing costs.

Figure 1:
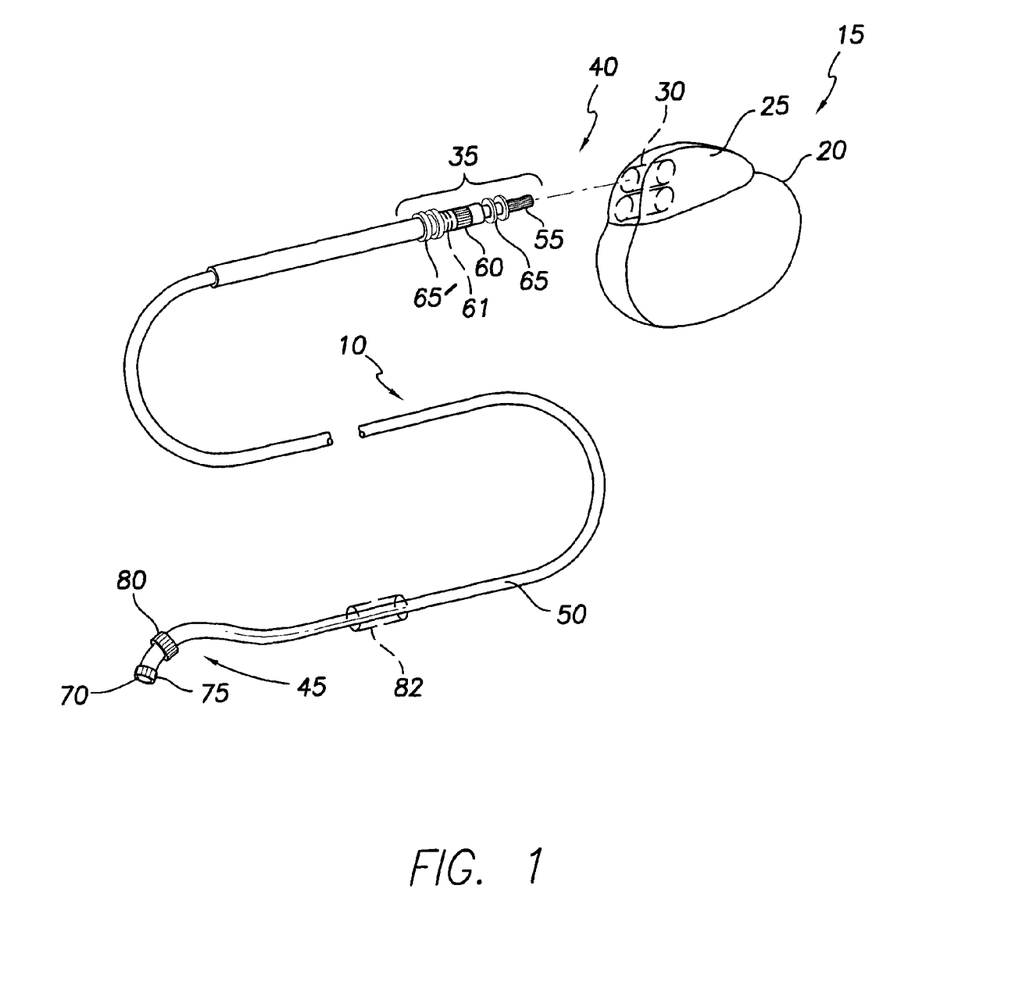
FIG. 1 is an isometric view of an implantable medical lead and a pulse generator for connection thereto.

For a general discussion of an embodiment of a lead 10 including a tube 120 swaged to an electrical conductor 100 to form a swaged assembly 130, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. The proximal end 40 may include a lead connector end 35 including a pin contact 55, a first ring contact 60, a second ring contact 61, which is optional, and sets of spaced-apart radial seals 65. In some embodiments, the lead connector end 35 may include the same or different seals and may include a greater or lesser number of contacts. For example, the lead connector end 35 may be in the form of an IS-1, IS-4, DF-1, etc. configuration. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIG. 1, in one embodiment, the lead distal end 45 may include a distal tip 70, a tip electrode 75 and a ring electrode 80. In some embodiments, the lead distal end 45 may include a helical anchor that is extendable from within the distal tip 70 for active fixation and may or may not act as an electrode. In other embodiments, the lead distal end 45 may include features or a configuration that facilitates passive fixation.

As shown in FIG. 1, in some embodiments, the distal end 45 may include a defibrillation coil 82 about the outer circumference of the lead body 50. The defibrillation coil 82 may be located proximal of the ring electrode 80.

As illustrated in FIG. 1 where the lead 10 is configured for passive fixation, the tip electrode 75 may form the distal tip 70 of the lead body 50. The ring electrode 80 may extend about the outer circumference of the lead body 50, proximal of the distal tip 70. In other embodiments, a distal end 45 configured for passive fixation may include a greater or lesser number of electrodes 75, 80 in different or similar configurations.

Where the lead 10 is configured for active fixation, an atraumatic tip may form the distal tip 70 of the lead body 50, and the helical anchor electrode may be extendable/retractable relative to the distal tip 70 through an opening in the distal tip 70. The ring electrode 80 may extend about the outer circumference of the lead body 50, proximal of the distal tip 70. In other embodiments, a distal end 45 configured for active fixation may include a greater or lesser number of electrodes in different or similar configurations.

In one embodiment, the tip electrode 75 or helical anchor electrode may be in electrical communication with the pin contact 55 via a first electrical conductor and the ring electrode 80 may be in electrical communication with the first ring contact 60 via a second electrical conductor. In some embodiments, the defibrillation coil 82 may be in electrical communication with the second ring contact 61 via a third electrical conductor. In yet other embodiments, other lead components (e.g., additional ring electrodes, various types of sensors, etc.) mounted on the lead body distal region 45 or other locations on the lead body 50 may be in electrical communication with a third ring contact (not shown) similar to the second ring contact 61 via a fourth electrical conductor.

Depending on the embodiment, electrical connections in a lead body 50 between an electrical conductor of the lead 10 and the electrical component or device 80 (e.g., an electrode for sensing or pacing, a defibrillation coil, a strain gage, a pressure sensor, an integrated chip, an inductor, etc.) of the lead 10 served by the electrical conductor may be accomplished via welding, crimping or a combination of welding and crimping. Welding is advantageous in that it results in a compact, electrically conductive, joint configuration between the electrical conductor and its electrical component 80. However, every weld-joint is accompanied by a mechanically compromised area of material directly adjacent to the weld. This area of material is known as a heat-affected zone ("HAZ"). The HAZ is often the weakest point of the welded construction, typically reducing metal mechanical strength by 40%-60% due to irreversible changes of the metal structure resulting from exposure to an intense heat cycle during the welding. The HAZ becomes susceptible to fatigue failure and failure under tensile loading, especially if unprotected via some form of strain relief.

In addition to the mechanical strength issues associated with the HAZ, the weld itself may contain intermetallic brittle structures which may reduce strength up to 90%. As a result, the weld construction itself may be unpredictably fragile. Thus, while in one embodiment of the lead 10 the mechanical/electrical connections between one or more of the electrical conductors and the respective electrical components or devices 80 may be achieved via welded joints, in a preferred embodiment, the mechanical/electrical connections between the electrical conductors and the respective electrical components or devices 80 may employ a strain relief component.

Figures 2A, 2B:
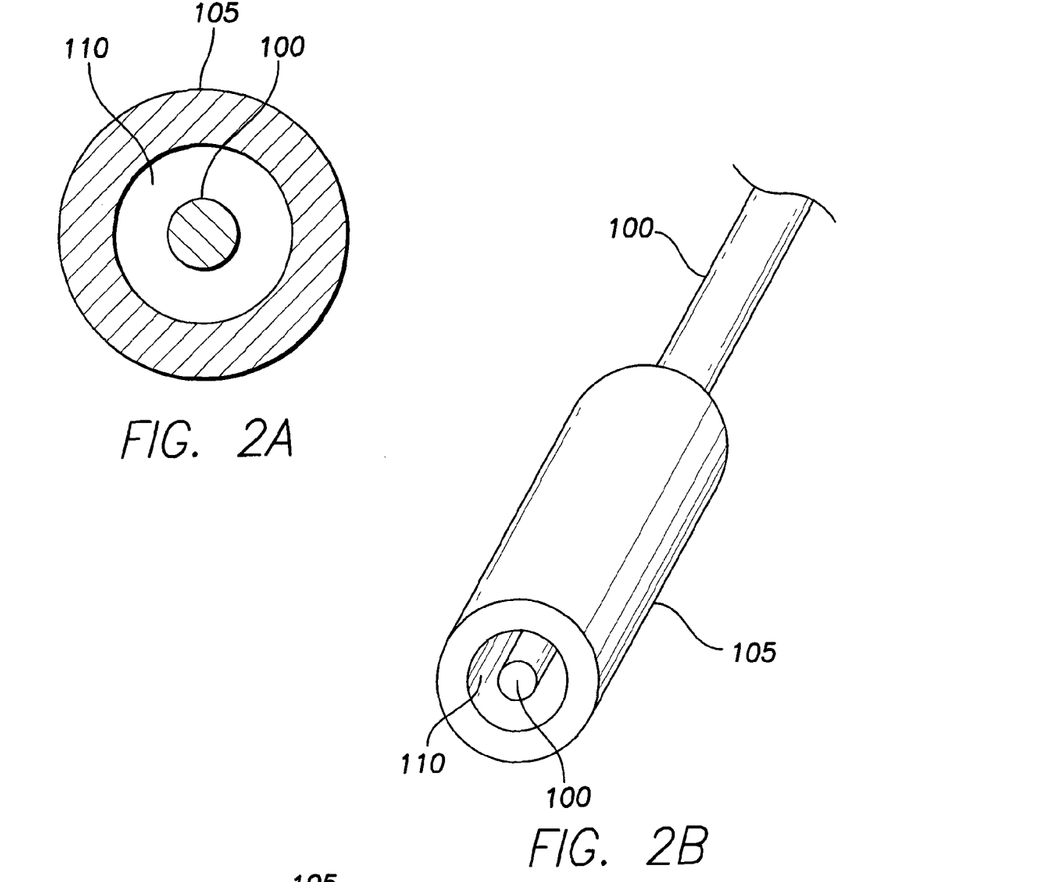
FIG. 2A is an end view of an electrical conductor extending into a non-crimped crimp slug.
FIG. 2B is an isometric view of an electrical conductor extending into a non-crimped crimp slug.

For a discussion of a first type of strain relief component, reference is now made to FIGS. 2A and 2B, which are, respectively, an end view and an isometric view of an electrical conductor 100 extending into a non-crimped crimp slug 105. As indicated in FIGS. 2A and 2B, in one embodiment, an electrical conductor 100 may be positioned within a central opening 110 of a crimp slug 105 in a non-crimped or collapsed state. The interior diameter of the non-crimped crimp slug 105 may substantially exceed the diameter of the electrical conductor 100 so as to facilitate the easy insertion of the electrical conductor 100 into the non-crimped crimp slug 105.

Figure 2C:
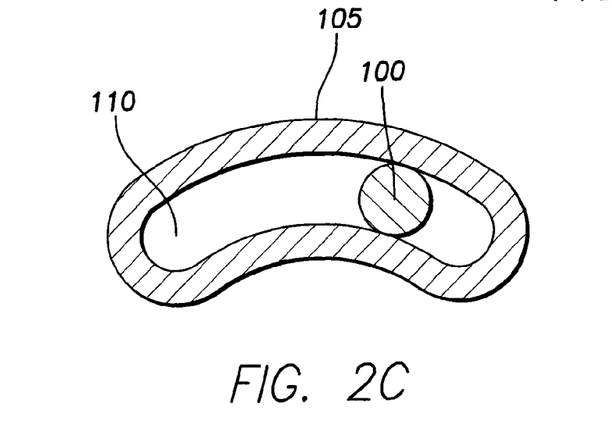
FIG. 2C is another end view of the crimp slug and electrical conductor of FIG. 2A, except the crimp slug is crimped on the electrical conductor.
Figure 2D:
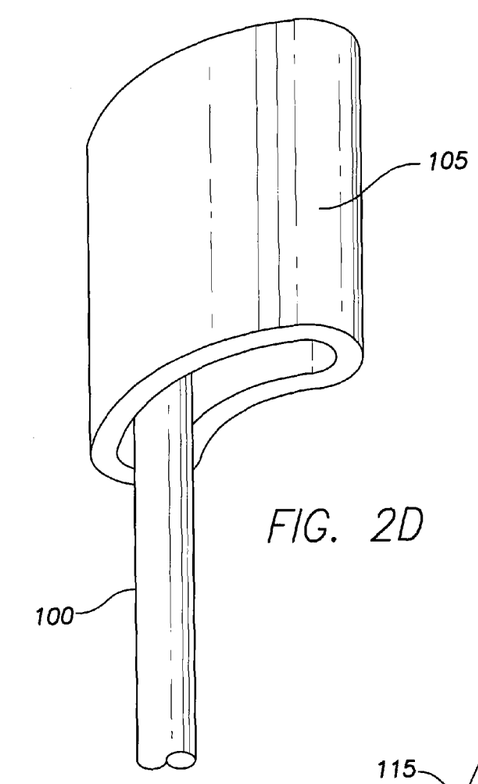
FIG. 2D is another isometric view of the crimp slug and electrical conductor of FIG. 2A, except the crimp slug is crimped on the electrical conductor.

As depicted in FIGS. 2C and 2D, which are similar respective views as FIGS. 2A and 2B, once the crimp slug 105 is positioned relative to the electrical conductor 100 such that the crimp slug 105 will be adjacent the respective electrical component 80 (e.g., an electrode for sensing or pacing, a defibrillation coil, a strain gage, a pressure sensor, an integrated chip, an inductor, etc.) when the lead 10 is assembled, the crimp slug 105 may be crimped or otherwise flattened onto the electrical conductor 100 to secure the electrical conductor 100 within and to the crimped crimp slug 105. The crimped crimp slug 105 may then be welded to the respective electrical component (e.g., electrodes 75, 80 or defibrillation coil 82 depicted in FIG. 1). This technique provides for a robust connection between the electrical conductor 100 and its respective electrical component. Also, the technique minimizes heat transfer to the material of the electrical conductor 100 and also immobilizes any portion of the electrical conductor 100 that could potentially be compromised by the weld operation, thereby protecting the cable conductor 100 from fatigue and tensile loading failures. The crimp slug 105 also provides a larger pad of material to incorporate into the weld, providing more metal for the laser weld. Therefore, employing crimp slugs 105 in the connection of the electrical conductor 100 to the respective electrical component offers several advantages over simple weld only connections.

Figure 2E:
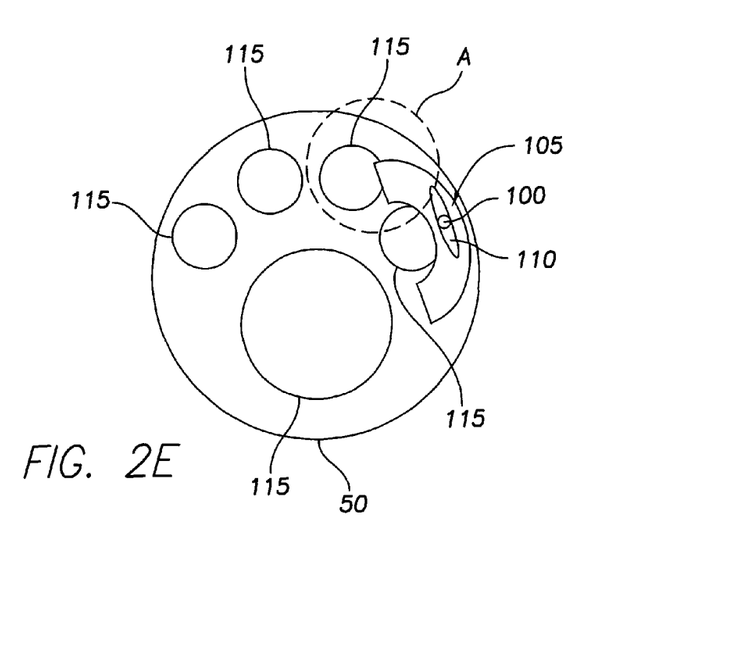
FIG. 2E is a transverse cross section of the lead body of FIG. 1, wherein an electrical conductor with a crimp tube crimped thereon as depicted in FIGS. 2C and 2D is routed through a lumen of the lead body.

As can be understood from FIGS. 2C and 2D, crimping significantly alters the shape and aspect-ratio of the crimp slug 105; making the crimp slug 105 substantially wider than the electrical conductor 100, which is not the case with a weld only connection between an electrical connector and its respective electrode. The substantial width of a crimped crimp slug 105 may facilitate welding to the electrode and weld strength due to having a wide generally curved surface that may abutted against the electrode during the welding process. The substantial width is not likely to be an issue for larger diameter leads 10 or leads 10 having a limited number of electrical conductors or other elements extending through the lead body 50. However, as can be understood from region A of FIG. 2E, which is a transverse cross section of the lead body 50 of FIG. 1, where the lead 10 has a small diameter or a substantial number of electrical conductors or other elements (e.g., lumens 115) extending through the lead body 50, the wideness of the crimped crimp slug 105 may result in the crimp slug 105 overflowing or otherwise crowding adjacent elements or structures 115 extending through the lead body 50.

Figure 3A:
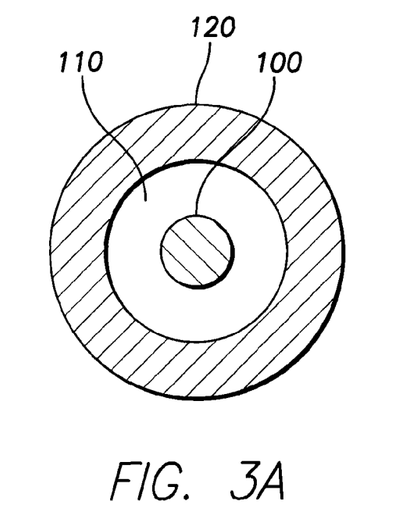
FIG. 3A is an end view of an electrical conductor extending into a non-swaged tube.
Figure 3B:
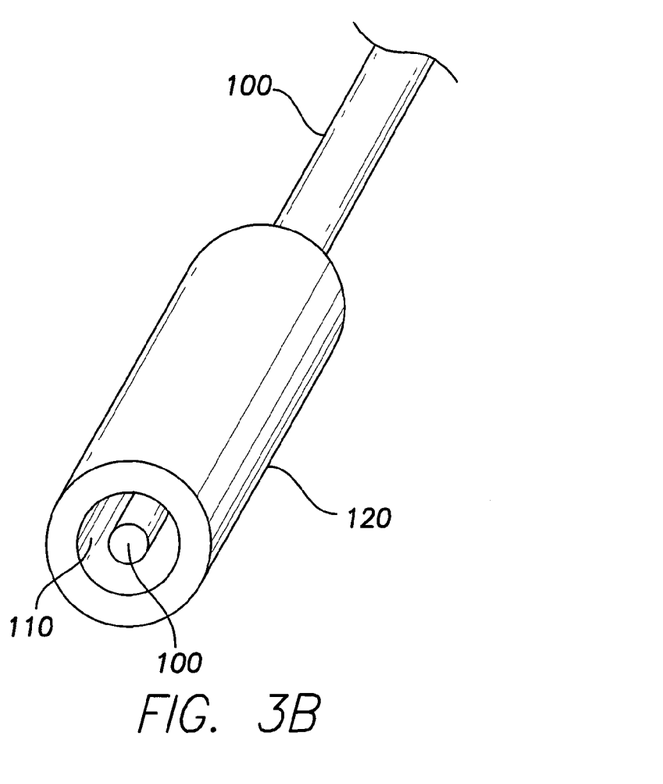
FIG. 3B is an isometric view of an electrical conductor extending into a non-swaged tube.

For a discussion of a preferred type of strain relief component that provides a robust connection between the electrical conductor 100 and the respective electrical component (e.g., an electrode for sensing or pacing, a defibrillation coil, a strain gage, a pressure sensor, an integrated chip, an inductor, etc.) while doing so with a diameter comparable to weld only connections, reference is now made to FIGS. 3A and 3B, which are, respectively, an end view and an isometric view of an electrical conductor 100 extending into a non-swaged tube 120. As indicated in FIGS. 3A and 3B, in one embodiment, an electrical conductor 100 may be positioned within a central opening 125 of a tube 120 in a non-swaged state. In one embodiment, the tube 120 may be a segment of hypo-tube 120 formed of platinum-iridium alloy, stainless steel or other appropriate electrically conductive material. For example, the segment of hypo-tube 120 may have a wall thickness range of between approximately 0.0025 inch and approximately 0.063 inch, an inside diameter range of between approximately 0.006 inch and approximately 0.15 inch, and an outside diameter range of between approximately 0.0123 inch and approximately 0.203 inch. As with the non-crimped crimp slug 105 illustrated in FIG. 2A, the interior diameter of the non-swaged tube 120 may substantially exceed the diameter of the electrical conductor 100 so as to facilitate the easy insertion of the electrical conductor 100 into the non-swaged tube 120.

Figure 3C:
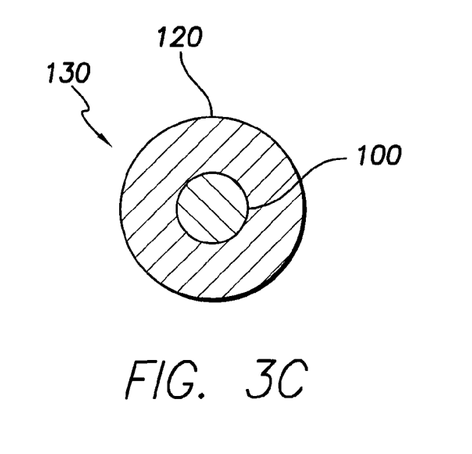
FIG. 3C is another end view of the electrical conductor extending into the tube of FIG. 3A, except the tube is swaged onto the electrical conductor.
Figure 3D:
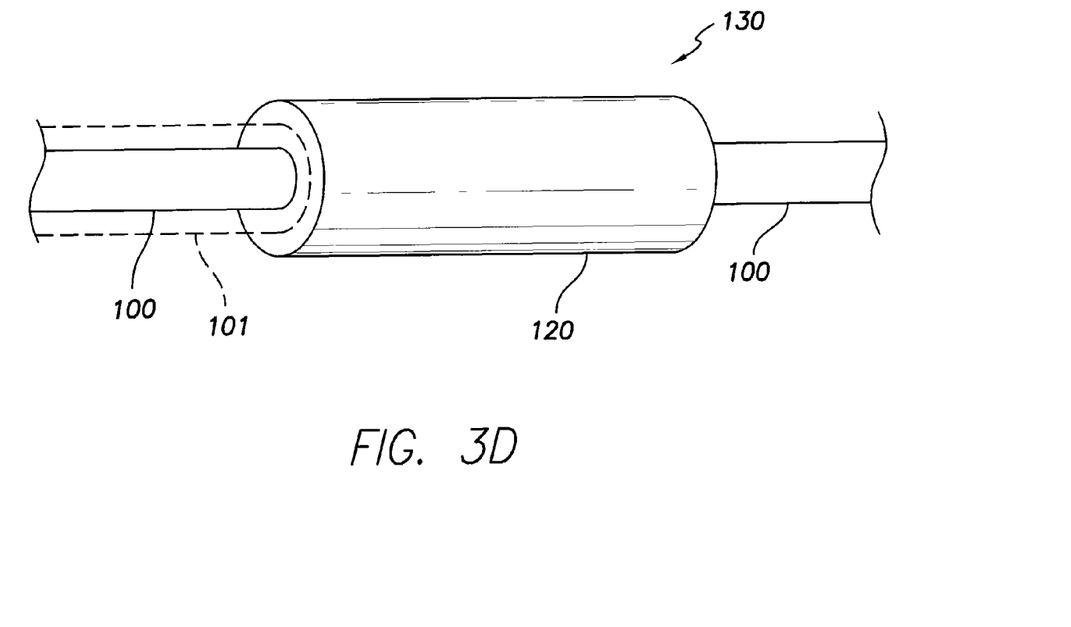
FIG. 3D is a side view of the electrical conductor extending into the tube of FIG. 3A, except the tube is swaged onto the electrical conductor.

As depicted in FIGS. 3C and 3D, which are, respectively, end and side views of the tube 120 and electrical conductor depicted in FIGS. 3A and 3B, once the tube 120 is positioned relative to the electrical conductor 100 such that the tube 120 will be adjacent the respective electrical component when the lead 10 is assembled, the tube 120 may be swaged onto and about the electrical conductor 100 to secure the electrical conductor 100 within and to the swaged tube 120. The swaged tube 120 may then be welded to the respective electrical component (e.g., electrodes 75, 80 or defibrillation coil 82 depicted in FIG. 1).

Swaging and, more specifically, rotary swaging, is a cold-working process used to reduce the diameter of a cylindrical work-piece 120 around an electrical conductor 100, such as, for example, a multi-filar cable conductor. In one embodiment, the swaging is achieved by using a split-die set that separates and closes at a very high rate, to hammer down the work-piece 120 in a circumferentially uniform fashion. Generally, swaging machines are commercially developed and available from companies such as Machine Solutions Inc. and Ft. Wayne Metals.

As can be understood from a comparison of FIGS. 3A and 3C, swaging is a technique where mechanical forces are applied to "shrink" the tube 120 circumferentially. The circumferential shrinking of the tube 120 is such that the tube 120 maintains its circular cross-section and snugly conforms to the outer circumference of the electrical conductor 100. In swaging the tube 120 to the electrical conductor 100 extending through the tube 120, a mechanical force is circumferentially applied to the co-axial system of multiple parts (i.e., the coaxial arrangement of the electrical connector 100 and the tube 120).

In one embodiment, as can be understood from a comparison of FIGS. 3A and 3C, the swaging process compresses the tube 120 onto the electrical conductor 100 in a generally uniformly circumferential manner so as to generate an interference fit between the joined components 100, 120. The resulting assembly 130 (i.e., joined components 100, 120) has a cross section that is generally uniformly circular and a diameter only slightly larger in diameter than the diameter of the electrical conductor 100.

The swaged assembly 130 may be attached to an electrical component (e.g., electrodes 75, 80 or defibrillation coil 82 of FIG. 1) via welding. As with crimp slugs 105, welding a swaged assembly 130 to an electrical component provides for a robust connection between the electrical conductor 100 and its respective electrical component. Also, the technique minimizes heat transfer to the material of the electrical conductor 100 and also immobilizes any portion of the electrical conductor 100 that could potentially be compromised by the weld operation, thereby protecting the cable conductor 100 from fatigue and tensile loading failures. The swaged assembly 130 also provides a larger pad of material to incorporate into the weld, providing more metal for the laser weld.

Figure 3E:
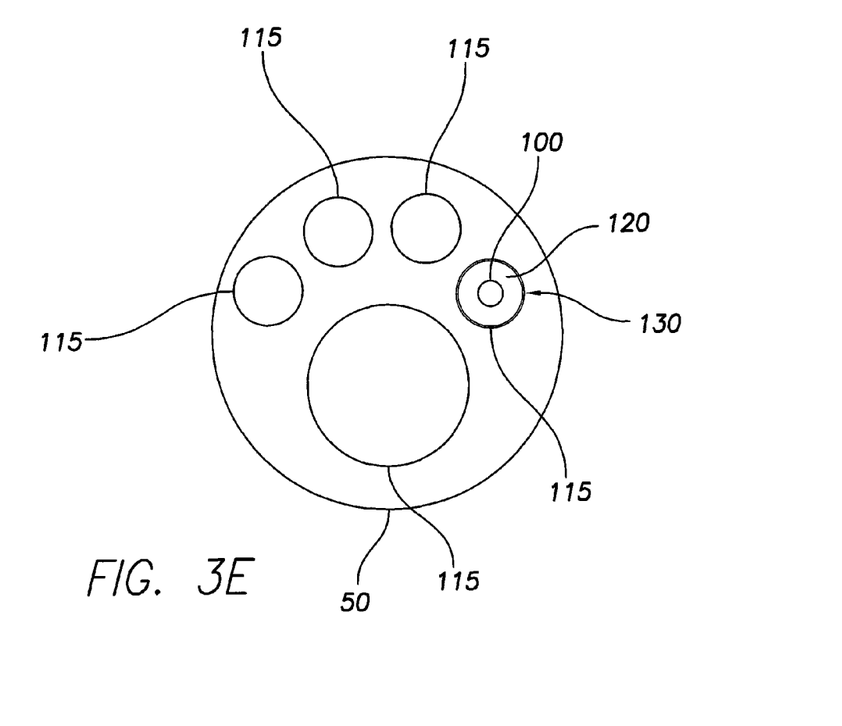
FIG. 3E is a transverse cross section of the lead body of FIG. 1, wherein an electrical conductor with a tube swaged thereon as depicted in FIGS. 3C and 3D is routed through a lumen of the lead body.

Also, as can be understood from FIG. 3E, which is a transverse cross section of the lead body 50 of FIG. 1, due to its small diameter and generally circular cross section, the swaged assembly 130 provides the size advantages of a weld only connection. In other words, as can be understood from a comparison of FIGS. 2E and 3E, the swaged assembly 130 is less likely to extend out of its lumen 115 to crowd, or overflow into, adjacent structures than a crimped crimp slug 105. The swaged assembly 130, on account of its small diameter, is less likely than a crimp slug 105 to require a large skive in the polymer lead body in order to access lumens for the conductor-electrical component terminations. The small diameter of the swaged assembly 130 facilitates maintaining good electrical isolation between lumens, as can be understood from FIG. 3E. These advantages offered by the swaged assembly 130 are useful for up and coming multi-electrode, "intelligent", and small diameter leads (e.g., leads 10 in the 3-4 Fr size range). Intelligent leads may be those lead designs that incorporate novel active components, such as sensors, integrated circuits, or drug delivery mechanisms.

Figure 4:
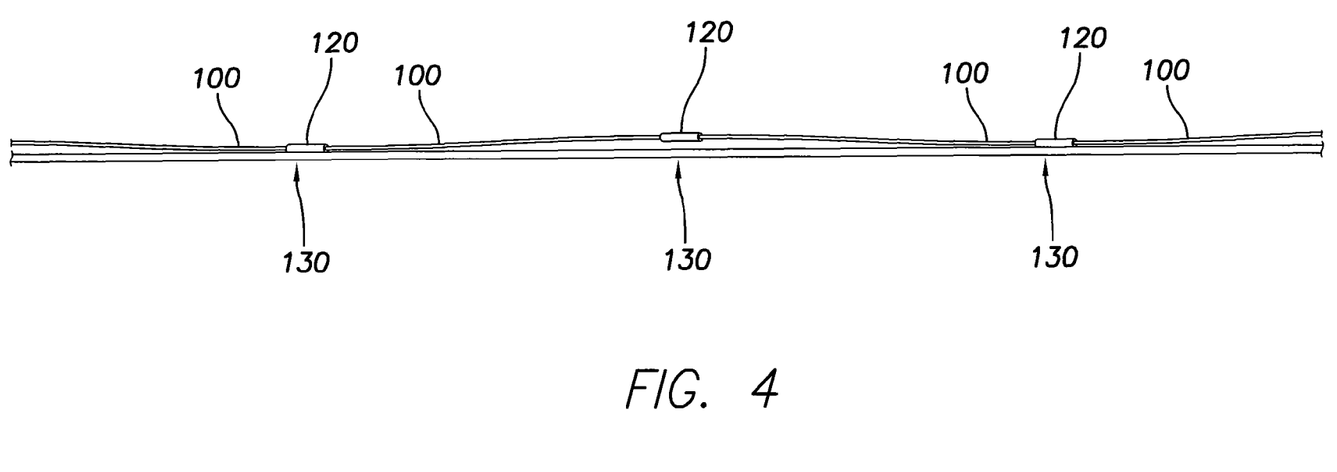
FIG. 4 is a side view of an electrical conductor prior to being threaded through a lumen of a lead body as depicted in FIG. 3E, wherein the electrical conductor has multiple tubes swaged thereon.

As can be understood from FIG. 4, which is a side view of an electrical conductor 100 prior to being threaded through a lumen 115 of a lead body 50 as depicted in FIG. 3E, multiple tubes 120 may be swaged onto the electrical conductor 100 an various intervals along the electrical conductor 100. Thus, in addition to providing a low profile welding connection for a single electrical component, the swaging technique disclosed herein also enables the connection of multiple electrical components to a single electrical conductor 100.

For example, the design of the certain St. Jude Medical multi-electrode leads may include the attachment of four or more electrodes to a single electrical conductor. To facilitate such an electrode arrangement, four or more tubes 120 may be swaged at regular or irregular intervals along the electrical conductor 100 to form four or more swage assemblies 130 that may be welded to respective electrodes.

Due to its small diameter, the swage assembly 130 facilitates an electrical conductor 100 with multiple swage assemblies 130 (see FIG. 4) to be prefabricated and then strung into the lead body, rather than assembling the components on the lead body. In other words, an electrical conductor 100 with swage assemblies 130 at regular intervals along the length of the electrical conductor 100 may be stored on a spool until needed for assembly of a lead. At such a time, a desired length of the stored electrical conductor 100 with its swage assemblies 130 may be removed from the spool and strung through a lead body. Such a process may substantially reduce manufacturing time and costs.

In one embodiment and as can be understood from FIGS. 3D, 5B, 6A and 6B, the electrical conductor 100 is coated with an ETFE jacket 101 that has an outer diameter of 0.009 inches. When attaching multiple swage assemblies 130 to a coated multi-filar cable 100, the insulation 101 may not need to be removed from the cable 100. Instead, only small regions, where the swaged tube 120 will attach to the cable 100, may need to be ablated with respect to the insulation 101. This maintains electrical insulation and improves manufacturing technique.

In one embodiment, the final swaged diameter of each Pt/Ir swage tube 120 may be 0.014 inches. Because of this low-profile design, the electrical conductor 100 with its four or more swage assemblies 130 may be strung through a lumen 115 of the lead body 50. By comparison, an electrical conductor 100 with four or more crimp slugs 105 would be nearly impossible to thread through a lumen 115 of a lead body. To complete the lead 10, each electrode, sensor, integrated chip, or other device to be electrically connected to the electrical conductor 100 may then be welded to the respective swage tube 120.

Figure 5A:
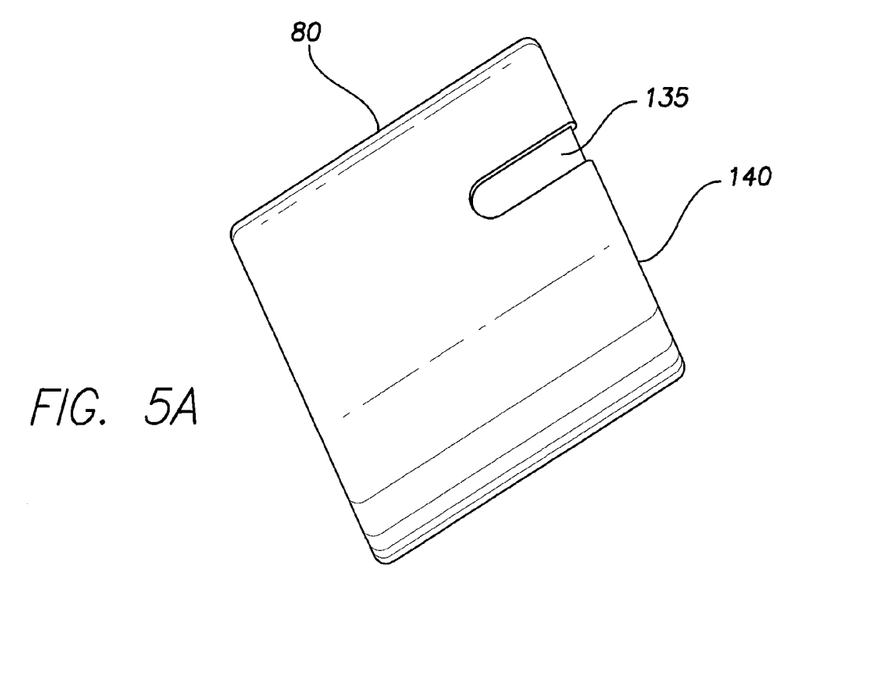
FIG. 5A is a side view of a ring electrode specifically configured for use with the swaged assembly of FIGS. 3C and 3D.
Figure 5B:
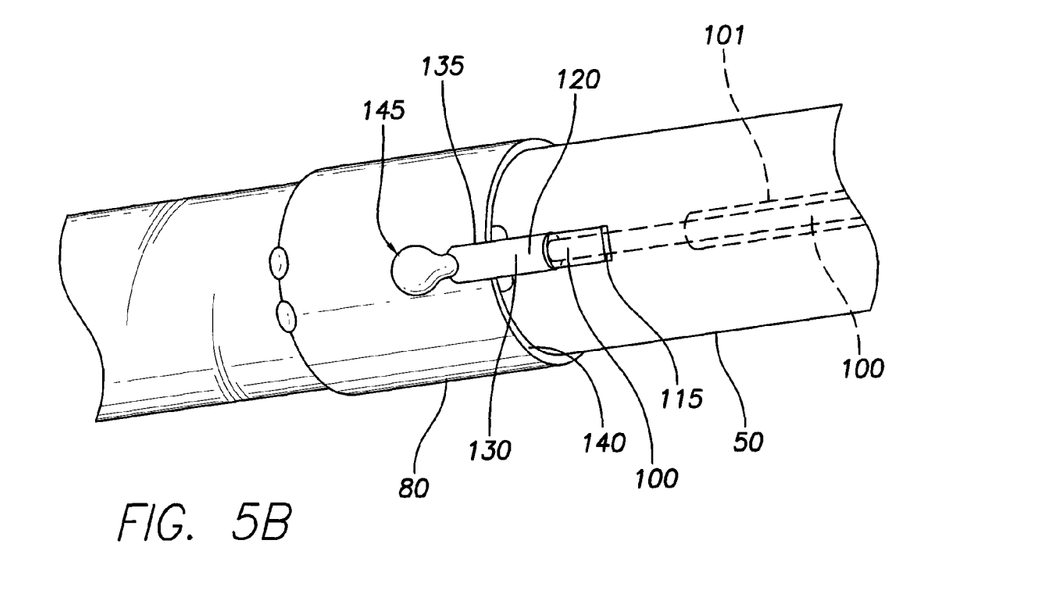
FIG. 5B is a side view of the ring electrode of FIG. 5A mounted on a lead body.

For a discussion of electrodes that may be specifically configured for use with the swaged assembly 130, reference is now made to FIGS. 5A and 5B, which are respectively a side view of a ring electrode 80 and the ring electrode 80 mounted on the lead body 50. As indicated in FIG. 5A, in one embodiment, the ring electrode 80 may employ a slot 135 that extends distally in a longitudinal manner a proximal edge 140 of the ring electrode 80. As depicted in FIG. 5B, the slot 135 receives the swaged assembly 130 in an aligned fashion. The tube 120 of the swaged assembly 130 is welded at one or more weld locations 145 to the edges of the ring electrode slot 135. The electrical conductor 100 extends proximally from the tube 120 and into a lumen 115 of the lead body 50.

Figure 6A:
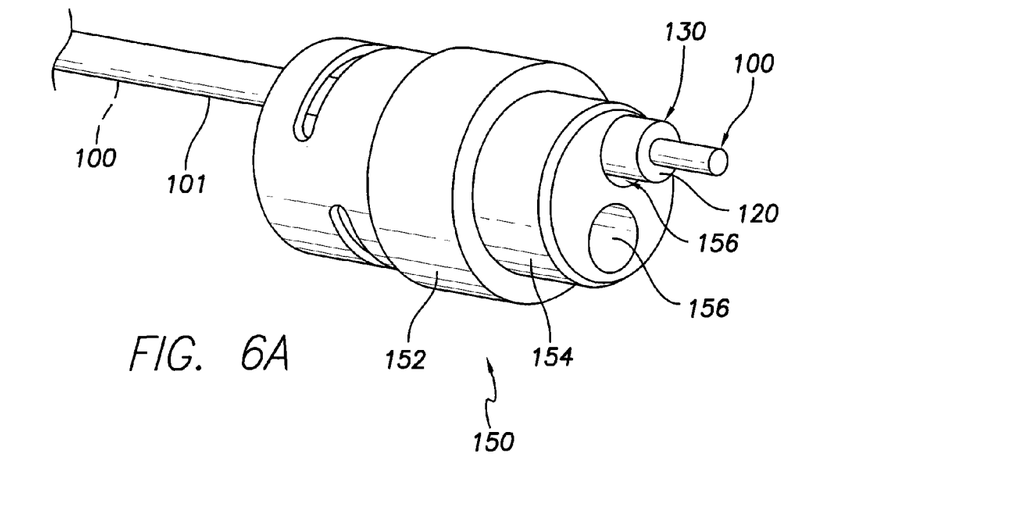
FIG. 6A is an isometric view of an electrode assembly specifically configured for use with the swaged assembly of FIGS. 3C and 3D.
Figure 6B:
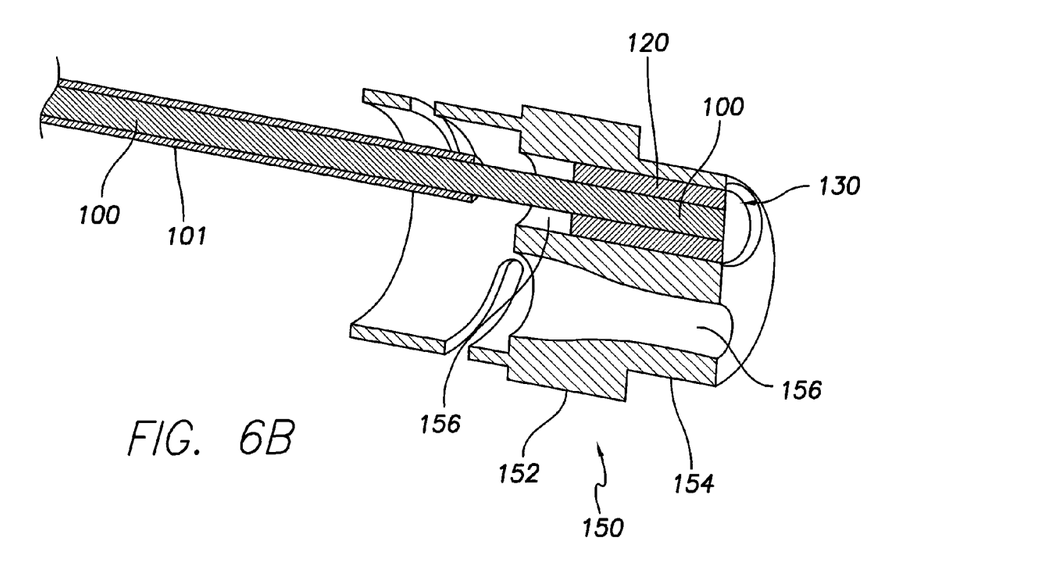
FIG. 6B is an isometric cross section of the electrode assembly depicted in FIG. 6A.

The swaged assembly 130 supports the use of other electrode assemblies that might not be possible absent the use of a swaged assembly 130. For example, as indicated in FIGS. 6A and 6B, which are, respectively, an isometric view and an isometric cross section of such an electrode assembly 150, the electrode assembly 150 may include a ring portion 152 radially extending from an inner cylindrical portion 154 that may be a generally solid cylindrically shaped core of electrically conductive metal, such as, for example, platinum, platinum-iridium alloy, etc. One or more lumens 156 may longitudinally extend through the inner cylindrical portion 154. The lumens 156 may be aligned with corresponding lumens of a lead body when the electrode assembly 150 is mounted in a lead body. When the electrode assembly 150 is mounted in the lead body, the ring portion 152 may resemble and act as a standard ring electrode.

A swaged assembly 130 may be inserted into a lumen 156 as indicated in FIGS. 6A and 6B. The tube 120 of the swaged assembly 130 may then be welded to the lumen 156 of the inner cylindrical portion 154, and the electrical conductor 100 extending from the swaged assembly 130 extends through the corresponding lead body lumen. As can be understood from FIG. 6A, the swaged assembly 130 may initially extend from the lumen 156 of the inner cylindrical portion 154, but, as indicated in FIG. 6B, the extending portion of the swaged assembly 150 may be laser melted or mechanically trimmed such that the swaged assembly 130 is generally flush with the end of the inner cylindrical portion 154.

Although the present invention has been described with reference to preferred embodiments, persons skilled in the art will recognize that changes may be made in form and detail without departing from the spirit and scope of the invention.

What is claimed is:

1. An implantable medical lead comprising:
a longitudinally extending body having a distal end and a proximal end;
a cable conductor extending through the body between the proximal end and the distal end;
an electrically conductive tube swaged about an outer circumferential portion of the cable conductor; and
a ring electrode on the body and electrically connected to the tube such that the cable conductor is electrically coupled to the ring electrode, the ring electrode having an outer surface;
wherein the ring electrode has a slot in which the tube is received, the slot being generally parallel to a longitudinal axis of the body and disposed on the outer surface of the ring electrode.

2. The lead of claim 1, wherein the tube is welded within the slot.

3. An implantable medical lead comprising:
a longitudinally extending body having a distal end and a proximal end;
a cable conductor extending through the body between the proximal end and the distal end;
an electrically conductive tube swaged about an circumference of the cable conductor; and
a ring electrode on the body and electrically connected directly to the tube such that the cable conductor is electrically coupled to the ring electrode;
wherein the ring electrode has an electrically conductive and generally solid cylindrical core portion and a ring portion radially extending from the core portion, the core portion having a lumen in which the tube is received, the lumen being generally parallel to a longitudinal axis of the body.

4. The lead of claim 3, wherein the tube is welded within the lumen.

5. The lead of claim 3, wherein the tube is rotary swaged about the outer circumferential surface of the electrical conductor.

6. The lead of claim 3, wherein the tube is a segment of hypo-tube.

7. The lead of claim 3, wherein the cable conductor has a solid core wire conductor or a multi-filar cable conductor.

8. The lead of claim 3, wherein the ring electrode is at least one of a pacing electrode and a sensing electrode.

9. A method of assembling an implantable medical lead, the method comprising:
providing an electrically conductive tube segment;
extending a cable conductor through a lumen of the tube segment;
swaging the tube segment about a portion of an outer circumferential surface of the cable conductor;
electrically connecting the tube segment to a ring electrode such that the cable conductor is electrically coupled to the ring electrode, the ring electrode having an outer surface; and
positioning tube segment in a slot of the ring electrode prior to electrically connecting the tube segment to the ring electrode, the slot disposed on the outer surface of the ring electrode.

10. The method of claim 9, further comprising extending the cable conductor through a lumen of a lead body after the tube segment has been swaged about the outer circumferential surface of the cable conductor.

11. The method of claim 9, wherein electrically connecting the tube segment to the ring electrode includes welding the tube segment within the slot.

12. A method of assembling an implantable medical lead, the method comprising:
providing an electrically conductive tube segment;
extending a cable conductor through a lumen of the tube segment;
swaging the tube segment about an outer circumferential surface of the cable conductor; and
providing a ring electrode having a generally solid cylindrical core portion and a ring portion radially extending from the core portion, the core portion having a lumen being generally parallel to a longitudinal axis of the lead;
electrically connecting the tube segment directly to the ring electrode such that the cable conductor is electrically coupled to the ring electrode; and
positioning the tube segment in the lumen of the ring electrode prior to electrically connecting the tube segment to the ring electrode.

13. The method of claim 12, wherein electrically connecting the tube segment to the ring electrode comprises welding the tube segment within the lumen of the electrode.

14. The method of claim 12, wherein the swaging comprises rotary swaging.

15. The method of claim 12, wherein the ring electrode is at least one of a pacing electrode and a sensing electrode.

\* \* \* \* \*